US00PP20536P2

(12) United States Plant Patent
Bergman

(10) Patent No.: US PP20,536 P2
(45) Date of Patent: Dec. 8, 2009

(54) ***CHRYSANTHEMUM* PLANT NAMED 'DARK YOCHATHAM'**

(50) Latin Name: *Chrysanthemum×morifolium*
Varietal Denomination: Dark Yochatham

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/283,268

(22) Filed: Sep. 8, 2008

(51) Int. Cl.
*A01H 5/00* (2006.01)

(52) U.S. Cl. ..... Plt./287

(58) Field of Classification Search ..... Plt./287
See application file for complete search history.

(56) References Cited

U.S. PATENT DOCUMENTS

PP17,493 P2 * 3/2007 Bergman ..... Plt./287
PP17,927 P2 * 8/2007 Bergman ..... Plt./287

OTHER PUBLICATIONS

Plant Varieties Journal #68, Jul. 2008. 112 pages. See especially p. 12.*

* cited by examiner

*Primary Examiner*—Wendy C. Haas
(74) *Attorney, Agent, or Firm*—C. A. Whealy

(57) ABSTRACT

A new and distinct cultivar of *Chrysanthemum* plant named 'Dark Yochatham', characterized by its compact, upright, outwardly spreading and uniformly mounded plant habit; moderately vigorous growth habit; freely branching habit; dark green-colored foliage; uniform, freely and early flowering habit; decorative-type inflorescences with violet-colored ray florets; and excellent postproduction longevity.

1 Drawing Sheet

Botanical designation: *Chrysanthemum×morifolium.*
Cultivar denomination: 'Dark Yochatham'.

CROSS-REFERENCED TO CLOSELY-RELATED APPLICATIONS

Title: *Chrysanthemum* Plant Named 'Orange Yochatham' U.S. Plant patent application Ser. No. 12/283,267 Applicant: Wendy R. Berman Filed: Concurrently with this application.

BACKGROUND OF THE INVENTION

The present invention relates to a new and distinct cultivar of *Chrysanthemum* plant, botanically known as *Chrysanthemum×morifolium*, commercially grown as a pot-type *Chrysanthemum* and hereinafter referred to by the name 'Dark Yochatham'.

The new *Chrysanthemum* is a naturally-occurring whole plant mutation of the *Chrysanthemum×morifolium* cultivar 'Yochatham', disclosed in U.S. Plant Pat. No. 17,927. The new *Chrysanthemum* was discovered and selected by the Inventor in a controlled greenhouse environment as a single flowering plant within a population of plants of 'Yochatham' in March, 2005, in Fort Myers, Fla.

Asexual reproduction of the new *Chrysanthemum* by vegetative tip cuttings was first conducted in a controlled greenhouse environment in Fort Myers, Fla. in June, 2005. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dark Yochatham'. These characteristics in combination distinguish 'Dark Yochatham' as a new and distinct pot-type *Chrysanthemum* cultivar:

1. Compact, upright, outwardly spreading and uniformly mounded plant habit.
2. Moderately vigorous growth habit.
3. Freely branching habit.
4. Dark green-colored foliage.
5. Uniform, freely and early flowering habit.
6. Decorative-type inflorescences with violet-colored ray florets.
7. Excellent postproduction longevity with inflorescences maintaining good substance and color for about five weeks in an interior environment.

Plants of the new *Chrysanthemum* differ from plants of the parent, 'Yochatham', in the following characteristics:

1. Plants of the new *Chrysanthemum* flower more uniformly than plants of 'Yochatham'.
2. Plants of the new *Chrysanthemum* and 'Yochatham' differ in ray floret color as plants of 'Yochatham' have light purple-colored ray florets.

Plants of the new *Chrysanthemum* can be compared to plants of *Chrysanthemum×morifolium* 'Orange Yochatham', disclosed in U.S. Plant patent application No. 12/283,267. Plants of the new *Chrysanthemum* differ primarily from plants of 'Orange Yochatham' in ray floret color as plants of 'Orange Yochatham' have orange bronze-colored ray florets.

Plants of the new *Chrysanthemum* can be compared to plants of *Chrysanthemum×morifolium* 'Deep Yopresidio', disclosed in U. S. Plant Pat. No. 17,493. In side-by-side comparisons conducted in Fort Myers, Fla., plants of the new *Chrysanthemum* primarily from plants of 'Deep Yopresidio' in the following characteristics:

1. Plants of the new *Chrysanthemum* were more compact than plants of 'Deep Yopresidio'.
2. Plants of the new *Chrysanthemum* had smaller inflorescences than plants of 'Deep Yopresidio'.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises side perspective view of typical flowering plants of 'Dark Yochatham' grown in a container.

The photograph at the top of the sheet is a close-up view of typical inflorescences of 'Dark Yochatham'.

DETAILED BOTANICAL DESCRIPTION

The aforementioned photographs and following observations and measurements describe plants grown in Leamington, Ontario, Canada during the late spring in a glass-covered greenhouse and under conditions and practices which approximate those generally used in commercial pot-type *Chrysanthemum* production. During the production of the plants, day temperatures ranged from 20° C. to 24° C., night temperatures ranged from 15° C. to 17° C. and light levels ranged from 4,000 to 6,000 foot candles. Four unrooted cuttings were directly stuck in 15-cm containers, exposed to long day/short night conditions, and pinched about two weeks later. One week after the pinch, the photoinductive short day/long night treatments were started. Plants used in the photographs and the description were grown as spray-types and were eleven weeks from planting. In the following description, color references are made to The Royal Horticultural Society Colour Chart, 2001 Edition, except where general terms of ordinary dictionary significance are used.

Botanical classification: *Chrysanthemum×morifolium* 'Dark Yochatham'.

Parentage: Naturally-occurring whole plant mutation of *Chrysanthemum×morifolium* 'Yochatham', disclosed in U.S. Plant Pat. No. 17,927.

Propagation:

*Type.*—Terminal vegetative cuttings.

*Time to initiate roots.*—About four days at temperatures of 21° C.

*Time to produce a rooted young plant.*—About ten days at temperatures of 21° C.

*Root description.*—Fine to thick, fibrous; white in color.

*Rooting habit.*—Freely branching; moderately dense.

Plant description:

*Appearance.*—Herbaceous decorative pot-type *Chrysanthemum* typically grown as a spray-type. Compact; stems upright and outwardly spreading giving a uniformly mounded appearance to the plant. Freely branching habit, about six lateral branches develop after removal of terminal apex (pinching); dense and full plant habit; moderately vigorous growth habit.

*Plant height.*—About 29 cm.

*Plant width.*—About 19 cm.

*Lateral branches.*—Length: About 26 cm. Diameter: About 4 mm. Internode length: About 2 cm. Strength: Strong. Texture: Pubescent; longitudinally ridged. Color: Close to 147B.

Foliage description:

*Arrangement.*—Alternate, simple.

*Length.*—About 5.5 cm.

*Width.*—About 4.2 cm.

*Shape.*—Palmately lobed.

*Apex.*—Cuspidate.

*Base.*—Attenuate.

*Margin.*—Palmately lobed, sinuses between lateral lobes parallel.

*Texture, upper and lower surfaces.* Fine pubescence; veins prominent on lower surface.

*Color.*—Developing leaves, upper surface: Close to N137B. Developing leaves, lower surface: Close to 137C. Fully expanded leaves, upper surface: Close to N137A; venation, close to 137B. Fully expanded leaves, lower surface: Close to 137B; venation, close to 137C.

*Petiole.*—Length: About 1.5 cm. Diameter: About 2.5 mm. Texture, upper and lower surfaces: Pubescent. Color, upper and lower surfaces: Close to 137C.

Inflorescence description:

*Appearance.*—Decorative-type inflorescence form with elongated oblong-shaped ray florets. Inflorescences borne on terminals above foliage. Ray florets arranged acropetally on a capitulum. Typically grown as a spray-type.

*Fragrance.*—Faint; spicy.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to two weeks of long day/short night conditions followed by photoinductive short day/long night conditions flower about eight weeks later.

*Postproduction longevity.*—Inflorescences maintain good color and substance for about five weeks in an interior environment; inflorescences persistent.

*Quantity of inflorescences.*—Freely flowering, about ten to eleven inflorescences develop per lateral stem.

*Inflorescence bud.*—Height: About 1.6 cm. Diameter: About 1.2 cm. Shape: Oblate. Color: Close to 76A.

*Inflorescence size.*—Diameter: About 4.8 cm. Depth (height): About 2.2 cm. Diameter of disc: About 3 mm. Receptacle height: About 5 mm. Receptacle diameter: About 1.8 cm. Receptacle color: Close to 147B.

*Ray florets.*—Shape: Elongated oblong. Orientation: Initially upright, then with development, close to perpendicular to peduncle. Aspect: Initially incurved, then mostly flat. Length: About 2.5 cm. Width: About 6 mm. Apex: Rounded or emarginate. Base: Attenuate; short corolla tube. Margin: Entire. Texture, upper and lower surfaces: Smooth, glabrous; satiny. Number of ray florets per inflorescence: About 156 arranged in about 14 whorls. Color: When opening, upper surface: Close to N80C. When opening, lower surface: Close to 76A. Fully opened, upper surface: Close to 84B; color becoming closer to 77D with development. Fully opened, lower surface: More grey than 76A; color does not fade with development.

*Disc florets.*—Arrangement: Massed at center of receptacle. Shape: Tubular, elongated. Apex: Five-pointed. Length: About 3 mm. Width: About 1 mm. Number of disc florets per inflorescence: About twelve. Color, immature: Apex: Close to 153C. Mid-section: Close to 153D. Base: Close to 145D. Color, mature: Apex: Close to 7A. Mid-section: Close to 7C. Base: Close to 155D.

*Phyllaries.*—Number of phyllaries per inflorescence: About 32 arranged in about two whorls. Length: About 1.2 cm. Width: About 2.5 mm. Shape: Narrowly elliptical. Apex: Acute. Base: Truncate. Margin: Entire. Texture, upper surface: Smooth, glabrous; waxy. Texture, lower surface: Pubescent. Color, upper surface: Close to N137B. Color, lower surface: Close to 147B.

*Peduncles.*—Length: About 4 cm to 5.8 cm. Diameter: About 2 mm. Angle: About 30° to 40° from vertical. Strength: Strong, flexible. Texture: Pubescent. Color: Close to 147B.

*Reproductive organs.*—Androecium: Present on disc florets only. Filament length: About 1 mm. Filament color: Close to 1C. Anther shape: Narrowly oblong. Anther length: About 1 mm. Anther color: Close to 13A. Pollen amount: None observed. Gynoecium: Present on both ray and disc florets. Pistil length: About 6 mm. Stigma shape: Bi-parted. Stigma color: Close to 2B. Style length: About 3 mm. Style color: Close to 145C. Ovary color: Close to 157D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* tolerate temperatures ranging from about 5° C. to about 40° C.

It is claimed:

1. A new and distinct *Chrysanthemum* plant named 'Dark Yochatham' as illustrated and described.

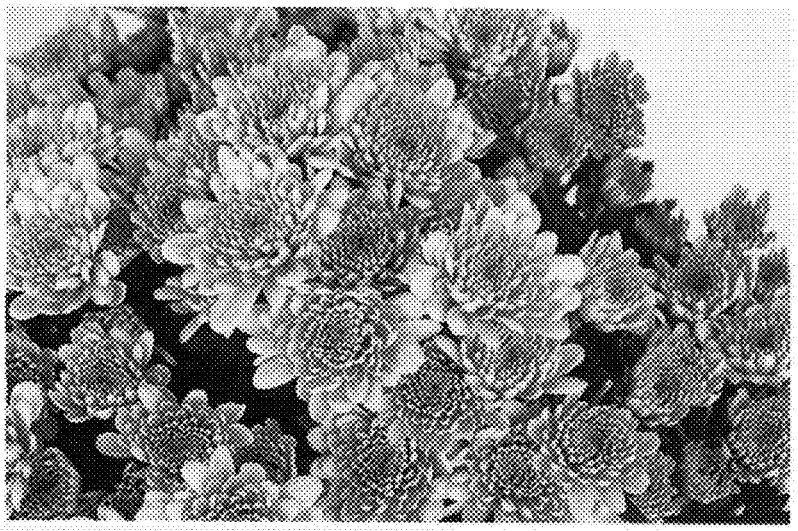
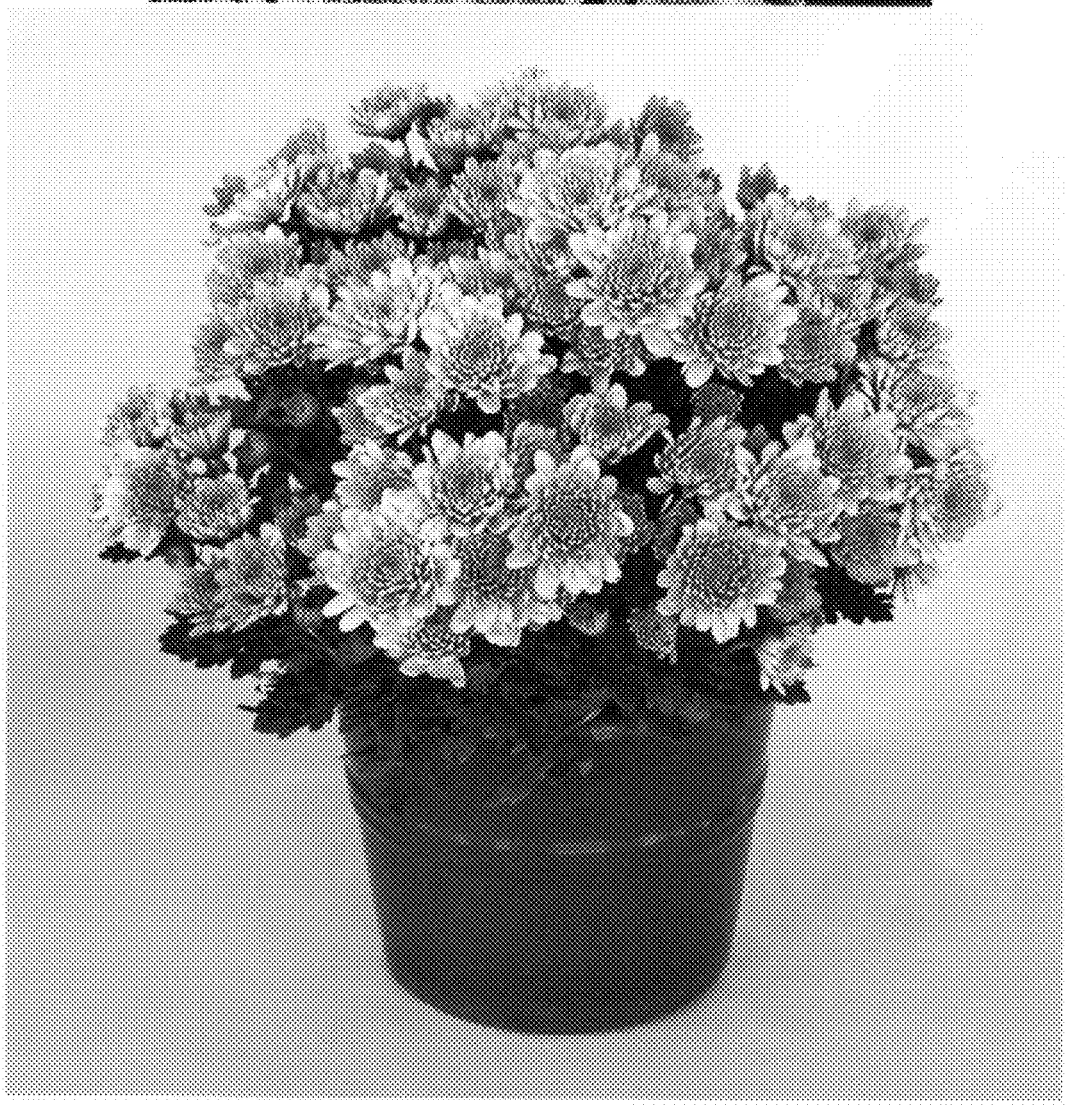

* * * * *